United States Patent [19]

Smith et al.

[11] Patent Number: 4,937,389

[45] Date of Patent: Jun. 26, 1990

[54] SEPARATION OF 3,3'4,4'- AND 2,3,3',4'-TETRAMETHYLDIPHENYL ETHER

[75] Inventors: Thomas G. Smith; John M. Weis, both of Naperville; Mark W. Meszaros, Batavia, all of Ill.

[73] Assignee: Amoco Corporation, Chicago, Ill.

[21] Appl. No.: 212,509

[22] Filed: Jun. 28, 1988

[51] Int. Cl.$^5$ .............................................. C07C 41/16
[52] U.S. Cl. .................................................. 568/635
[58] Field of Search ......................... 568/635; 260/707

[56] References Cited

U.S. PATENT DOCUMENTS 2,493,781  1/1950  Schneider et al. ................. 568/756

OTHER PUBLICATIONS

Vogel, Arthur, "A Textbook of Practical Organic Chemistry" 3rd ed. 1965, pp. 122-130.

*Primary Examiner*—Bruce Gray
*Attorney, Agent, or Firm*—James R. Henes; William H. Magidson; Ralph C. Medhurst

[57] ABSTRACT

A method of separating 3,3',4,4'-tetramethyldiphenyl ether from its solid mixture with 2,3,3',4'-tetramethyldiphenyl ether.

17 Claims, No Drawings

SEPARATION OF 3,3'4,4'- AND 2,3,3',4'-TETRAMETHYLDIPHENYL ETHER

BACKGROUND OF THE INVENTION

1. Field of the Invention

This invention relates to the separation of tetramethyldiphenyl ether isomers and more particularly concerns the separation of 3,3',4,4'-tetramethyldiphenyl ether from a solid mixture thereof with 2,3,3',4'-tetramethyldiphenyl ether.

2. Description of the Prior Art

Over approximately the past two decades, organic compounds in which two or more carboxylic acid groups are bonded to one or more carboxylic and/or heterocyclic aromatic nuclei have become of increasing interest, either as direct components in or as intermediates for synthetic condensation polymer molecules. Some of the polymers containing repeating units derived from aromatic polycarboxylic acids have found broad spectrum utility in synthetic fibers and films, as well as in various types of resin formulations, whereas others of such polymers have been more limited in scope of application, but are not less useful. The more common nuclei of aromatic polycarboxylic acids that form polymers that are useful for these purposes include certain simple and more complex bridged aromatic ring systems. One important member of the group involving bridged aromatic ring systems can be pictured most simply by the formula: Ar—O—Ar$^1$, where the groups, Ar and Ar$^1$, represent the same or different cyclic aromatic nuclei. In some cases, the aromatic nuclei of such polycarboxylic acids will contain one or more additional ring substituents, such as amino, nitro, halogen, hydroxyl, cyano, sulfonyl, and the like groups. These additional groups do not participate in the principal polymer-forming reactions, but they can be desirable molecular constituents, either because of the properties they impart to the polymer or because they render the initial polymer molecules susceptible to modification by further reaction.

The aromatic polycarboxylic acids used in polymers generally are produced by subjecting aromatic compounds having a plurality of appropriately positioned alkyl substituents on the aromatic ring or rings to oxidation processes. Thus, the commercial importance of diphenyl ether-based monomers and diphenyl sulfide-based monomers in engineering polymer formulations is well recognized. Either such materials are themselves potentially useful monomers or can serve as precursors to monomers of proven utility such as oxybisanaline. For example, 4,4'-diaminodiphenyl ether is currently used in the preparation of Torlon ® and of Vespel ®. Other diphenyl ether-based monomers which are of potential commercial importance include diacids, diols or dianhydrides of diphenyl ether.

Although diphenyl ether-based monomers and diphenyl sulfide-based monomers have proven utility, their high cost and the lack of a convenient method of preparation have hindered any large volume applications of such monomers. For example, 3,3',4,4'-tetracarboxydiphenyl ether is useful as the precursor to oxybis (phthalic anhydride), a monomer used in the formulation of polyimides and can be produced by the oxidation of 3,3',4,4'tetramethyldiphenyl ether using an oxygen-containing gas and a metal-containing catalyst. One attractive method for producing 3,3',4,4'-tetramethyldiphenyl ether is the Ullmann coupling reaction between 4-bromo-o-xylene and an alkali metal phenolate of 3,4-dimethylphenol. However, because of the presence of 3-bromo-o-xylene as an impurity with 4-bromo-o-xylene, this reaction generally produces substantial amounts of 2,3,3',4'-tetramethyldiphenyl ether as a by-product, in addition to the desired 3,3',4,4'-tetramethyldiphenyl ether, and it is extremely difficult to separate these two isomers. In fact, no method for effecting this separation has been reported. Thus, it would be very desirable to develop a convenient and efficient method for separating 3,3',4,4'tetramethyldiphenyl ether from 2,3,3',4'-tetramethyldiphenyl ether.

OBJECTS OF THE INVENTION

It is therefore a general object of the present invention to provide an improved method for the convenient and efficient separation of 3,3',4,4'-tetramethyldiphenyl ether from 2,3,3',4'-tetramethyldiphenyl ether.

Other objects and advantages of the invention will become apparent upon reading the following detailed description and appended claims.

SUMMARY OF THE INVENTION

These objects are achieved by an improved method for separating 3,3',4,4'-tetramethyldiphenyl ether from a starting solid mixture thereof with 2,3,3',4'-tetramethyldiphenyl ether, comprising: (a) heating the aforesaid starting solid mixture comprising 3,3',4,4'-tetramethyldiphenyl ether to a temperature in the range of from about 38° C. to about 48° C. to thereby melt the mixture to form a liquid solution; (b) mixing the resulting liquid solution with a lower molecular weight monohydroxy alcohol in a weight ratio of from about 0.1 to about 2 parts of the alcohol per part of the liquid mixture and at a temperature in the range of from about 40° C. to about 46° C. to thereby form an ether phase and a separate alcohol phase; (c) cooling the aforesaid two liquid phases to a temperature in the range of from about 10° C. to about 25° C. to thereby crystallize, with vigorous mixing, 3,3',4,4'-tetramethyldiphenyl ether from the ether phase and thereby form a solid phase containing a substantially lower concentration of 2,3,3',4'-tetramethyldiphenyl ether than was present in the aforesaid starting solid mixture; and (d) separating the resulting solid phase.

The present invention is also a method for separating 3,3',4,4'-tetramethyldiphenyl ether from a starting solid mixture thereof with 2,3,3',4'-tetramethyldiphenyl ether, comprising: (a) mixing the aforesaid starting solid mixture comprising 3,3',4,4'-tetramethyldiphenyl ether and 2,3,3',4'-tetramethyldiphenyl ether with a lower molecular weight monohydroxy alcohol in a weight ratio of from about 0.1 to about 2.0 parts of the alcohol per part of the starting solid mixture; (b) heating the resulting solid mixture to a temperature in the range of from about 38° C. to about 48° C. to thereby melt the mixture of form an ether phase and a separate alcohol phase; (c) cooling the aforesaid two liquid phases to a temperature in the range of from about 10° C. to about 25° C. to thereby crystallize, with vigorous mixing, 3,3',4,4'-tetramethyldiphenyl ether from the ether phase and thereby form a solid phase containing a substantially lower concentration of 2,3,3',4'-tetramethyldiphenyl ether than present in the starting solid mixture; and (d) separating the resulting solid phase.

DETAILED DESCRIPTION OF THE INVENTION INCLUDING PREFERRED EMBODIMENTS

The method of the present invention is useful for the separation and purification of 3,3',4,4'tetramethyldiphenyl ether from a solid mixture thereof with 2,3,3',4'-tetramethyldiphenyl ether. The mixture contains preferably at least 50 weight percent up to about 95 weight percent, and more preferably at least 75 weight percent, of 3,3',4,4'-tetramethyldiphenyl ether. Preferably the solid mixture contains from about 5 weight percent to about 50 weight percent, more preferably up to about 25 weight percent of 2,3,3',4'-tetramethyldiphenyl ether. Preferably the solid mixture consists essentially of 3,3',4,4'-tetramethyldiphenyl ether and 2,3,3',4'-tetramethyldiphenyl ether and is free of other materials (a) that have a substantial effect on the solubility of either 3,3',4,4'-tetramethyldiphenyl ether or 2,3,3',4'-tetramethyldiphenyl ether in the alcohol or (b) that do not melt and form a liquid solution with 3,3',4,4'-tetramethyldiphenyl ether and 2,3,3',4'-tetramethyldiphenyl ether at a temperature in the range of from about 38° C. to about 48° C.

The method of the present invention can be initiated in either of two alternative approaches. In the first alternative, the aforesaid solid mixture is heated to a temperature in the range of from about 38° C., preferably from about 40° C., to about 48° C., preferably to about 46° C., to thereby melt the mixture to form a liquid solution. The resulting liquid solution is then mixed with the aforesaid lower molecular weight alcohol, preferably methanol, in a weight ratio of from about 0.1, preferably from about 0.3, to about 2.0, preferably to about 1.0 parts of the alcohol per part of the liquid solution by weight and at a temperature up to about 48° C., preferably up to about 46° C., to thereby form an ether phase and a separate alcohol phase.

In the second alternative, the aforesaid solid mixture is initially mixed with the aforesaid alcohol in a weight ratio of from about 0.1, preferably from about 0.3, to about 2.0, preferably to about 1.0, parts of the aforesaid alcohol per part of the solid mixture by weight, and the resulting slurry is heated to a temperature in the range of from about 38° C., preferably from about 40° C., to about 48° C., preferably to about 46° C., to thereby melt the solid mixture to form an ether phase and a separate alcohol phase.

Thereafter, regardless of which of the aforesaid two alternatives is employed, the resulting two liquid phases are cooled to a temperature in the range of from about 10° C., preferably from about 15° C., to about 25° C., preferably to about 20° C., to thereby crystallize with vigorous mixing, 3,3',4,4'-tetramethyldiphenyl ether from the ether phase and form a solid phase containing a substantially lower concentration, preferably less than 10 weight percent, more preferably less than 5 weight percent, of the 2,3,3',4'-tetramethyldiphenyl ether present in the aforesaid starting solid mixture. The resulting solid phase is then separated by means of any convenient solid-liquid separation technique such as centrifugation, filtration or vacuum suction.

Following separation, any 2,3,3',4'-tetramethyldiphenyl ether remaining with the 3,3',4,4'tetramethyldiphenyl ether crystals exists primarily as a coating on the crystals and can be substantially removed by washing the crystals at least once with a lower molecular weight monohydroxy alcohol, preferably methanol or by vacuum suction of the crystals. The alcohol wash solution is at a temperature in the range of from about 10° C., preferably from about 15° C., to about 30° C., preferably to about 25° C.

The present invention will be more clearly understood from the following specific examples.

EXAMPLES 1-44

Each of Examples 1-44 was performed using a sample which was a mixture of 3,3',4,4'- and 2,3,3'4'-tetramethyldiphenyl ether. The sample weighed 10 grams and contained 74.4 weight percent of 3,3',4,4'-tetramethyldiphenyl ether and 25.6 weight percent of 2,3,3',4'-tetramethyldiphenyl ether in Examples 1-9. In Example 10, the sample weighted 75 grams and contained 74.3 weight percent of 3,3',4,4'-tetramethyldiphenyl ether and 24.4 weight percent of 2,3,3,',4'-tetramethyldiphenyl ether. In each of Examples 11-44, the sample weighed 10 grams and had a 3,3',4,4'-tetramethyldiphenyl ether content indicated in Tables 2-4.

In each of Examples 1-44, except for Examples 18-26, the aforesaid sample was liquefied by heating to a temperature of 43° C. and then mixed vigorously with a solvent at a solvent-to-sample weight ratio indicated in Tables 1-4 and at a temperature of 43° C. Methanol was employed as the solvent in Examples 1-26, and the solvent employed in each of Examples 27-44 is indicated in Table 4. The resulting two liquid phases were mixed vigorously for from about 5 minutes to about 15 minutes. At 43° C., the 3,3',4,4'-tetramethyldiphenylether is not soluble in methanol, but the 2,3,3',4'-tetramethyldiphenylether is soluble. Thereafter the temperature of the mixture of liquid was reduced to 20° C. unless otherwise indicated in Tables 1-4, and 3,3',4,4'-tetramethyldiphenyl ether crystallized and was separated from the methanol phase by centrifugation. The contents of 3,3',4,4'- and 2,3,3',4'-tetramethyldiphenyl ethers and the yield of 3,3',4,4'-tetramethyldiphenyl ether in each Example are indicated in Tables 1-4. In Examples 18-26, the solid from a crystallization was washed at 20° C. with methanol.

TABLE 1

| Example No. | Solvent: Feed Wt. Ratio | Crystallization Crystal Purity (Wt. %) 3,3',4,4'- TMDPE | 2,3,3',4'- TMDPE | Yield of 3,3',4,4'- TMDPE |
|---|---|---|---|---|
| 1 | 1:1 | 88.5 | 11.1 | 84.9 |
| 2 | 0.5:1 | 88.1 | 11.8 | 87.3 |
| 3 | 0.5:1 | 89.6 | 10.3 | 85.1 |
| 4 | 0.4:1 | 92.3 | 7.6 | 85.2 |
| 5 | 0.3:1 | 90.6 | 9.6 | 86.7 |
| 6 | 0.3:1 | 94.8 | 5.1 | 85.8 |
| 7 | 0.75:1 | 87.4 | 12.5 | 84.3 |
| 8 | 0.75:1 | 86.7 | 12.9 | 88.6 |
| 9 | 0.75:1 | 83.5 | 16.0 | 90.1 |
| 10 | 0.3:1 | 92.7 | 7.3 | 88.9 |

TABLE 2

| Example No. | 3,3',4,4'- TMDPE in Feed (Wt. %) | Crystallization Solvent: Feed Wt. Ratio | Crystal Purity (Wt. %) 3,3',4,4'- TMDPE | Yield of 3,3',4,4'- TMDPE |
|---|---|---|---|---|
| 11 | 90.4 | 1:1 | 96.7 | 93.9 |
| 12 | 90.4 | 1:1 | 96.4 | 94.8 |
| 13 | 90.4 | 1:1 | 97.9 | 97.1 |
| 14 | 90.4 | 1:1 | 97.6 | 97.0 |
| 15 | 90.4 | 2:1 | 98.4 | 91.1 |
| 16 | 88.4 | 1:1 | 97.9 | 94.6 |

TABLE 2-continued

| | Crystallization | | Crystal Purity (Wt. %) | |
| --- | --- | --- | --- | --- |
| Example No. | 3,3',4,4'-TMDPE in Feed (Wt. %) | Solvent: Feed Wt. Ratio | 3,3',4,4'-TMDPE | Yield of 3,3',4,4'-TMDPE |
| 17 | 97.9 | 1:1 | 98.6 | 98.4 |

TABLE 3

Solvent Washing of Crystals

| Example No. | 3,3',4,4'-TMPDE in Feed (Wt. %) | Solvent: Feed Wt. Ratio | Crystal Purity (Wt. %) 3,3',4,4'-TMDPE | Crystal Purity (Wt. %) 2,3,3',4'-TMDPE | Yield of 3,3',4,4'-TMDPE |
| --- | --- | --- | --- | --- | --- |
| 18 | 88.1 | 2:1 | 96.0 | 4.0 | 94.7 |
| 19 | 89.6 | 2:1 | 95.4 | 4.6 | 89.7 |
| 20 | 88.5 | 1.5:1 | 94.7 | 5.3 | 92.2 |
| 21 | 90.6 | 1:1 | 93.5 | 6.5 | 98.5 |
| 22 | 90.6 | 1:1 | 94.7 | 5.3 | 97.0 |
| 23 | 92.3 | 1:1 | 95.0 | 5.0 | 96.7 |
| 24 | 86.7 | 1:1 | 92.4 | 7.6 | 99.2 |
| 25 | 83.5 | 1:1 | 92.1 | 7.9 | 95.8 |
| 26 | 80.4 | 1:1 | 92.2 | 7.8 | 95.8 |

TABLE 4

| Example No. | Solvent | 3,3',4,4'-TMDPE in Feed (Wt. %) | Solvent:Feed Wt. Ratio |
| --- | --- | --- | --- |
| 27 | o-xylene | 76.9 | 0.33:1 |
| 28 | o-xylene | 76.9 | 0.50:1 |
| 29 | o-xylene | 76.9 | 0.33:1 |
| 30 | o-xylene | 76.9 | 0.33:1 |
| 31 | o-xylene | 76.9 | 0.20:1 |
| 32 | o-xylene | 76.9 | 0.50:1 |
| 33 | o-xylene | 76.9 | 0.33:1 |
| 34 | o-xylene | 76.9 | 0.50:1 |
| 35 | o-xylene | 76.9 | 0.33:1 |
| 36 | o-xylene | 91.2 | 0.20:1 |
| 37 | o-xylene | 89.0 | 0.40:1 |
| 38 | o-xylene | 90.0 | 0.33:1 |
| 39 | o-xylene | 94.6 | 0.37:1 |
| 40 | 95% HOAc | 76.9 | 0.50:1 |
| 41 | 95% HOAc | 97.3 | 1:1 |
| 42 | 95% HOAc | 95.6 | 2:1 |
| 43 | 95% HOAc | 76.9 | 0.4:1 |
| 44 | 70% HOAc | 76.9 | 1:1 |

| Example No. | Crystal Purity (Wt. %) 3,3',4,4'-TMDPE | Crystal Purity (Wt. %) 2,3,3',4'-TMDPE | Yield of 3,3',4,4'-TMDPE |
| --- | --- | --- | --- |
| 27 | 87.8 | 12.1 | 28.5[1] |
| 28 | 89.9 | 10.1 | 26.6[1] |
| 29 | 94.6 | 5.3 | 57.8[2] |
| 30 | 90.2 | 9.8 | 59.6[3] |
| 31 | 89.8 | 10.1 | 64.5[3] |
| 32 | 93.2 | 6.7 | 37.4[3] |
| 33 | 91.2 | 8.8 | 69.8[2] |
| 34 | 91.8 | 7.4 | 50.8[4] |
| 35 | 92.1 | 7.8 | 73.8[4] |
| 36 | 95.6 | 4.6 | 97.0[2] |
| 37 | 95.6 | 4.3 | 61.2[1] |
| 38 | 94.6 | 4.3 | 74.4[3] |
| 39 | 97.4 | 2.4 | 63.5[2] |
| 40 | 92.3 | 7.6 | 75.1[2] |
| 41 | 95.6 | 4.3 | 67.0 |
| 42 | 96.4 | 7.6 | 72.4 |
| 43 | 80.3 | 19.6 | 88.0[5] |
| 44 | 78.1 | 21.8 | 83.5[1] |

Footnotes:
[1] Crystallized at 21° C.
[2] Crystallized at 16° C.
[3] Crystallized at 13° C.
[4] Crystallized at 4° C.
[5] Crystallized at 10° C.

The resulting 3,3',4,4'-tetramethyldiphenyl ether crystals were vacuum suctioned for 3-16 hours in Examples 4,6 and 11-16, were washed with methanol at 20° C. in Examples 17-26 and 41-42, or were crystallized from o-xylene or acetic acid at the temperature indicated in Table 4 for Examples 27-40 and 43-44.

The results of Examples 1-10 illustrate that a methanol-feed weight ratio as low as 0.3:1 is effective.

If the temperature at which the procedure is carried out is too low, e.g., below 38° C., the TMDPE isomer mixture will not melt. If the temperature is too high, e.g., above 49° C., then the 3,3',4,4'-TMDPE isomer becomes soluble in the methanol and subsequent cooling will not induce crystallization. Thus, there is a window of feasible temperatures for which the process is effective in producing high purity 3,3'-4,4'-TMDPE in high yield.

It has also been observed that during crystallization, a high stirring rate is desirable to achieve high purity crystals. With good mixing, smaller crystals are formed which may prevent the 2,3,3',4'-isomer from being trapped within the crystal structure.

The results of Examples 11-17 illustrate that the invention is effective in producing very high purity crystals.

The results of Examples 18-26 illustrate that washing the crystals with methanol is effective in improving purity. These crystals are being formed in the TMDPE isomer layer, not in the methanol. As this crystallization from the melt proceeds, the 2,3,3',4'-isomer continues to dissolve in the methanol phase. When the crystals are separated from the mother liquor, any 2,3,3',4'-isomer remaining with the crystals exists primarily as a coating on the high purity 3,3',4,4'-TMDPE crystal. Thus, washing with methanol, or vacuum suction, or centrifugation is very effective in removing this layer of 2,3,3',4'-TMDPE with little loss of 3,3',4,4'-TMDPE, supporting the argument that the 2,3,3',4'-isomer is primarily on the crystal surface.

The results of Examples 27-44 illustrate that two other commonly used solvents, o-xylene and acetic acid, were markedly inferior to methanol. Alcohols other than methanol would be effective but the yields would vary.

From the above description, it is apparent that the objects of the present invention have been achieved. While only certain embodiments have been set forth, alternative embodiments and various modifications will be apparent from the above description to those skilled in the art. These alternatives are considered equivalents and within the spirit and scope of the present invention.

Having described the invention, what is claimed is:

1. A method for separating 3,3',4,4,'-tetramethyldiphenyl ether from a starting solid mixture thereof with 2,3,3',4'-tetramethyldiphenyl ether comprising:
   (a) heating the aforesaid starting solid mixture comprising 3,3',4,4'-tetramethyldiphenyl ether and 2,3,3',4'-tetramethyldiphenyl ether to a temperature in the range of from 38° C. to about 48° C. to thereby melt the mixture to form a liquid solution;
   (b) mixing the resulting liquid solution with methanol in a weight ratio of from about 0.1 to about 2 parts of methanol per part of the liquid solution and at a temperature in the range of about 38° C. to about 48° C. such that the resulting ether phase and methanol phase remain as two distinct liquid phases;
   (c) cooling the aforesaid two liquid phases to a temperature in the range of from about 10° C. to about 25° C. to thereby crystallize, with mixing, 3,3',4,4'-tetramethyldiphenyl ether from the ether phase and thereby form a phase of solid 3,3',4,4'-tetramethyldiphenyl ether containing a substantially lower concentration of 2,3,3',4'-tetramethyldiphenyl ether than present in the aforesaid starting solid mixture; and (d) separating the resulting solid phase formed in step (c) from the remaining liquid phases.

2. The method of claim 1 wherein the starting solid mixture, contains from about 50 to about 95 weight percent of 3,3',4,4'-tetramethyldiphenyl ether and from about 5 to about 50 weight percent of 2,3,3',4'-tetramethyldiphenyl ether.

3. The method of claim 2 wherein the starting solid mixture contains at least about 75 weight percent of 3,3',4,4'-tetramethyldiphenyl ether.

4. The method of claim 1 wherein the aforesaid starting solid mixture is heated in step (a) to a temperature in the range of from about 40° C. to about 46° C.

5. The method of claim 1 wherein the liquid solution formed in step (a) is mixed in step (b) with from about 0.3 to about 1 part of methanol per part of the liquid solution.

6. The method of claim 1 wherein the liquid solution formed in step (a) is mixed in step (b) at a temperature in the range of from about 40° C. to about 46° C.

7. The method of claim 1 wherein the two liquid phases remaining in step (b) are cooled in step (c) to a temperature in the range of from about 15° C. to about 20° C.

8. The method of claim 1 wherein the phase of solid 3,3',4,4'-tetramethyldiphenyl ether formed in step (c) contains less than 10 weight percent of 2,3,3',4'-tetramethyldiphenyl ether.

9. The method of claim 1 wherein 2,3,3',4'-tetramethyldiphenyl ether is present on the solid phase separated in step (d), and the solid phase is washed with methanol or vacuum suctioned to substantially remove from the surface thereof the 2,3,3',4'-tetramethyldiphenyl ether.

10. A method for separating 3,3',4,4'-tetramethyldiphenyl ether from a starting solid mixture thereof with 2,3,3',4'-tetramethyldiphenyl ether, comprising:

(a) mixing, the aforesaid starting solid mixture comprising 3,3',4,4'-tetramethyldiphenyl ether and 2,3,3',4'-tetramethyldiphenyl ether with methanol in a weight ratio of from about 0.1 to about 2.0 parts of methanol per part of the starting solid mixture;

(b) heating the resulting solid liquid mixture to a temperature in the range of from about 38° C. to about 48° C. to thereby melt the solid such that the resulting ether phase and methanol phase remain as two distinct liquid phases;

(c) cooling the aforesaid two liquid phases to a temperature in the range of from about 10° C. to about 25° C. to thereby crystallize, with mixing, 3,3',4,4'-tetramethyldiphenyl ether from the ether phase and form a phase of solid 3,3',4,4'-tetramethyldiphenyl ether containing a substantially lower concentration of 2,3,3',4'-tetramethyldiphenyl ether than present in the aforesaid starting solid mixture; and (d) separating the resulting solid phase formed in step (c) from the remaining liquid phases.

11. The method of claim 10 wherein the starting solid mixture contains from about 50 to about 95 weight percent of 3,3',4,4'-tetramethyldiphenyl ether and from about 5 to about 50 weight percent of 2,3,3'4'-tetramethyldiphenyl ether.

12. The method of claim 11 wherein the starting solid mixture contains at least about 75 weight percent of 3,3',4,4'-tetramethyldiphenyl ether.

13. The method of claim 10 wherein the starting solid mixture is mixed in step (a) with from about 0.3 to about 1.0 parts of methanol per part of the liquid solution.

14. The method of claim 10 wherein the solid-liquid mixture formed in step (a) is heated in step (b) at a temperature in the range of from about 40° C. to about 46° C.

15. The method of claim 10 wherein the two liquid phases formed in step (b) are cooled in step (c) to a temperature in the range of from about 15° C. to about 20° C.

16. The method of claim 10 wherein the phase of solid 3,3',4,4'-tetramethyldiphenyl ether formed in step (c) contains less than 10 weight percent of 2,3,3',4'-tetramethyldiphenyl ether.

17. The method of claim 10 wherein 2,3,3',4'-tetramethyldiphenyl ether is present in the solid phase separated in step (d), and the solid phase is washed with methanol or vacuum suctioned to substantially remove from the surface thereof the 2,3,3',4'-tetramethyldiphenyl ether.

* * * * *

UNITED STATES PATENT OFFICE
CERTIFICATE OF CORRECTION

Patent No. 4,937,389          Dated June 26, 1990

Inventor(s) Thomas G. Smith, John M. Weis, Mark W. Meszaros

It is certified that error appears in the above-identified patent and that said Letters Patent is hereby corrected as shown below:

| Col. | Line | |
|---|---|---|
| 2 | 11 | "3,3'4,4'tetramethyldiphenyl" should read --3,3',4,4'-tetramethyldiphenyl-- |
| 2 | 60 | "of form" should read --to form-- |
| 6 | 13 | "3,3-4,4'-TMDPE" should read --3,3',4,4'-TMDPE-- |
| 7 | 9 | "mixture, contains" should read --mixture contains-- |
| 7 | 45 | "mixing, the" should read --mixing the-- |

Signed and Sealed this

First Day of October, 1991

Attest:

HARRY F. MANBECK, JR.

Attesting Officer     Commissioner of Patents and Trademarks